(12) United States Patent
Sinha et al.

(10) Patent No.: US 8,735,438 B2
(45) Date of Patent: *May 27, 2014

(54) SUBSTITUTED-ARYL-2-PHENYLETHYL-1H-IMIDAZOLE COMPOUNDS AS SUBTYPE SELECTIVE MODULATORS OF ALPHA 2B AND/OR ALPHA 2C ADRENERGIC RECEPTORS

(75) Inventors: Santosh C. Sinha, Ladera Ranch, CA (US); Todd M. Heidelbaugh, Fountain Valley, CA (US); Smita Bhat, Irvine, CA (US); Ken Chow, Newport Coast, CA (US); Michael Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 12/966,560

(22) Filed: Dec. 13, 2010

(65) Prior Publication Data

US 2011/0077274 A1    Mar. 31, 2011

Related U.S. Application Data

(62) Division of application No. 11/971,829, filed on Jan. 9, 2008, now Pat. No. 7,902,247.

(51) Int. Cl.
*A61K 31/4164* (2006.01)
*C07D 233/54* (2006.01)

(52) U.S. Cl.
USPC ............. 514/397; 548/335.1; 548/343.1; 514/385; 514/396

(58) Field of Classification Search
USPC ......... 548/300.1, 335.1, 343.1; 514/385, 396, 514/397
See application file for complete search history.

(56) References Cited

U.S. PATENT DOCUMENTS

| | | | |
|---|---|---|---|
| 5,559,141 A | 9/1996 | Karjalainen et al. | |
| 6,313,172 B1 | 11/2001 | Chow et al. | |
| 7,902,247 B2 * | 3/2011 | Sinha et al. | 514/396 |
| 8,063,231 B2 * | 11/2011 | Fang et al. | 548/331.5 |
| 8,071,636 B2 * | 12/2011 | Fang et al. | 514/399 |
| 8,227,499 B2 * | 7/2012 | Sinha et al. | 514/397 |

FOREIGN PATENT DOCUMENTS

| | | |
|---|---|---|
| EP | 0 390 558 | 9/1994 |
| EP | 0390558 | 9/1994 |
| GB | 1499485 | 2/1978 |
| GB | 2101114 | 1/1983 |
| WO | WO920073 A1 | 1/1992 |
| WO | WO99/28300 | 6/1999 |
| WO | WO9928300 | 6/1999 |
| WO | WO01/00586 | 1/2001 |
| WO | WO0100586 | 1/2001 |
| WO | WO01/00586 | 1/2002 |
| WO | WO0100586 | 1/2002 |
| WO | WO02/076950 | 10/2002 |
| WO | WO02076950 | 10/2002 |
| WO | WO2007/085556 | 8/2007 |

OTHER PUBLICATIONS

Galley et al. (2007): STN International HCAPLUS database, (Columbus, Ohio), Accession number: 2007:845761.*
Messier et al, Pharmacol. Toxicol. 76, pp. 308-311-1995.
Conklin et al, Nature 363: pp. 274-6-1993.
"Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 497-557.
Galley et al (2007): STN International HCAPLUS database, (Columbus, Ohio), Accession number: 2007:845761.
Karjalainen et al (2000): STN International HCAPLUS database, (Columbus, Ohio), Accession number: 2000:505881.
Robert R. Ruffolo, Jr., Alpha-Adrenoreceptors: Molecular Biology, Biochemistry and Pharmacology, (Progress in Basic and Clinical Pharmacology series, Karger, 1991).
Messier et ai, Pharmacol. Toxicol. 76, pp. 308-311-1995.
Conklin et ai, Nature 363: pp. 274-6-1993.
"Prod rugs and Drug Delivery Systems," which is a chapter in Richard B. Silverman, Organic Chemistry of Drug Design and Drug Action, 2d Ed., Elsevier Academic Press: Amsterdam, 2004, pp. 497-557.

* cited by examiner

*Primary Examiner* — Golam M M Shameem
(74) *Attorney, Agent, or Firm* — Doina G. Ene

(57) ABSTRACT

A compound having selective modulating activity at the alpha 2B and/or alpha 2C adrenergic receptor subtypes is represented by the general Formula 1:

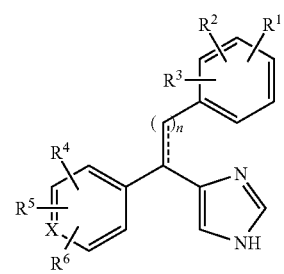

wherein
n=1-4;
X is C or N;
$R^1$-$R^6$ can be the same or different and are independently selected from the group consisting of H, $C_{1-6}$ alkyl, $OCH_3$, OH, F, Cl, Br, $CH_2OH$, $CH_2N(R^7)_2$, $C(O)R^8$, $CH_2CN$, $CF_3$,
wherein $R^7$ is H or $C_{1-6}$ alkyl; and
$R^8$ is $C_{1-6}$ alkyl or aryl.
The compounds of Formula 1 can be incorporated in pharmaceutical compositions and used in methods of treatment of alpha 2 receptor mediated diseases and conditions.

5 Claims, No Drawings

SUBSTITUTED-ARYL-2-PHENYLETHYL-1H-IMIDAZOLE COMPOUNDS AS SUBTYPE SELECTIVE MODULATORS OF ALPHA 2B AND/OR ALPHA 2C ADRENERGIC RECEPTORS

CROSS-REFERENCE TO RELATED APPLICATION

This application is a Divisional of U.S. patent application Ser. No. 11/971,829, filed Jan. 9, 2008, of which is incorporated herein by reference in its entirety.

FIELD OF THE INVENTION

Disclosed herein generally are subtype selective modulators of the alpha 2B and/or alpha 2C receptors useful for preparing pharmaceutical compositions.

BACKGROUND OF THE INVENTION

Alpha 2 adrenergic receptors have been characterized by molecular and pharmacological methods which include alpha 1A, alpha 1B, alpha 2A, alpha 2B and alpha 2C. Activation of these alpha receptors evokes physiological responses. Adrenergic modulators described in this disclosure activate one or both of the alpha 2B and/or alpha 2C receptors and have useful therapeutic actions.

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation, are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, beta 1, and beta 2 subtypes. Functional differences between alpha 1 and alpha 2 receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the alpha 1 subtype was reported. The alpha 1/alpha 2 selectivity of this compound was disclosed as being significant because agonist stimulation of the alpha 2 receptors was said to inhibit secretion of epinephrine and norepinephrine, while antagonism of the alpha 2 receptor was said to increase secretion of these hormones. Thus, the use of non-selective alpha-adrenergic blockers, such as phenoxybenzamine and phentolamine, was said to be limited by their alpha 2 adrenergic receptor mediated induction of increased plasma catecholamine concentration and the attendant physiological sequelae (increased heart rate and smooth muscle contraction). For a further general background on the alpha adrenergic receptors, attention is directed to Robert R. Ruffolo, Jr., Alpha-Adrenoreceptors: Molecular Biology, Biochemistry and Pharmacology, (Progress in Basic and Clinical Pharmacology series, Karger, 1991), wherein the basis of alpha 1/alpha 2 subclassification, the molecular biology, signal transduction, agonist structure-activity relationships, receptor functions, and therapeutic applications for compounds exhibiting alpha adrenergic receptor affinity is explored.

The cloning, sequencing and expression of alpha receptor subtypes from animal tissues has led to the subclassification of the alpha 1 adrenoreceptors into alpha 1A, alpha 1B, and alpha 1D. Similarly, the alpha 2 adrenoreceptors have also been classified alpha 2A, alpha 2B, and alpha 2C receptors. Each alpha 2 receptor subtype appears to exhibit its own pharmacological and tissue specificities. Compounds having a degree of specificity for one or more of these subtypes may be more specific therapeutic agents for a given indication than an alpha 2 receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha 2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these derivatives are said to be useful in the treatment of conditions such as hypertension, depression or pain.

International patent applications WO01/00586 published on Jan. 4, 2002 and WO99/28300 published on Jun. 10, 1999 describe certain imidazole derivatives acting as agonists of alpha 2B and/or alpha 2C adrenergic receptors. U.S. Pat. No. 6,313,172 discloses phenylmethyl-thiourea derivatives used for treatment of pain.

SUMMARY OF THE INVENTION

Disclosed herein generally are substituted-aryl-2-phenylethyl-1H-imidazole compounds as subtype selective modulators of alpha 2B and/or alpha 2C adrenergic receptors that includes compounds represented by Formula 1:

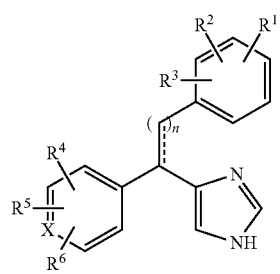

wherein
n=1-4;
X is C or N;

$R^1$-$R^6$ can be the same or different and are independently selected from the group consisting of H, $C_{1-6}$ alkyl, $OCH_3$, OH, F, Cl, Br, $CH_2OH$, $CH_2N(R^7)_2$, $C(O)R^8$, $CH_2CN$, $CF_3$, wherein $R^7$ is H or $C_{1-6}$ alkyl; and $R^8$ is $C_{1-6}$ alkyl or aryl.

Further disclosed herein are pharmaceutical compositions containing a pharmaceutical carrier and a therapeutically effective amount of substituted-aryl-2-phenylethyl-1H-imidazole compounds as subtype selective modulators of alpha 2B and/or alpha 2C adrenergic receptors which includes a compound represented by Formula 1.

Further disclosed are methods comprising administering to a mammal the present substituted-aryl-2-phenylethyl-1H-imidazole compounds as subtype selective modulators of alpha 2B and/or alpha 2C adrenergic receptors, for treating glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, Parkinson's ALS, and other neurodegenerative diseases.

DETAILED DESCRIPTION OF THE INVENTION

The general structures of exemplary specific subtype modulators of alpha 2B and/or alpha 2C adrenergic receptors which are used in the present pharmaceutical compositions and methods of treatment are provided by the general Formulas, below.

In one aspect of the disclosure, a compound having selective modulating activity at the alpha 2B and/or alpha 2C adrenergic receptors is represented by Formula 1:

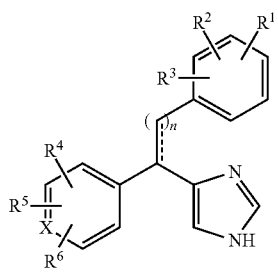

wherein
n=1-4;
X is C or N;
$R^1$-$R^6$ can be the same or different and are independently selected from the group consisting of H, $C_{1-6}$ alkyl, $OCH_3$, OH, F, Cl, Br, $CH_2OH$, $CH_2N(R^7)_2$, $C(O)R^8$, $CH_2CN$, $CF_3$, wherein $R^7$ is H or $C_{1-6}$ alkyl; and $R^8$ is $C_{1-6}$ alkyl or aryl.

In another aspect of the disclosure, in the compound of Formula 1, none of $R^1$ to $R^6$ is attached at the para position.

In the compound of Formula 1, n can be 1 or 2 and the $C_{1-6}$ alkyl can be methyl.

In another aspect of the disclosure, a compound is represented by Formula 2:

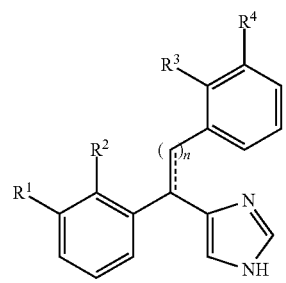

Formula 2 wherein $R^1$-$R^4$ can be same or different and are independently selected from the group consisting of H, $C_{1-6}$ alkyl, $OCH_3$, OH, F, Cl, Br, $CH_2OH$, $CH_2N(R^5)_2$, $C(O)R^6 CH_2CN$, and $CF_3$;

wherein $R^5$ is H or $C_{1-6}$ alkyl; and $R^6$ is $C_{1-6}$ alkyl or aryl.

Alternatively, in the compound of Formula 2, n can be 1 or 2, and the $C_{1-6}$ alkyl can be methyl.

In another aspect of the disclosure, a compound is represented by Formula 3:

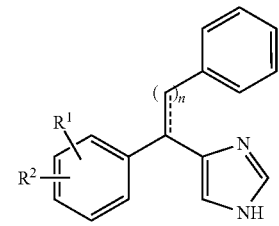

Formula 3

$R^1$-$R^2$ can be same or different and are independently selected from the group consisting of H, $CH_3$, $C_{1-6}$ alkyl, $OCH_3$, OH, F, Cl, Br, $CH_2OH$, $CH_2N(R^3)_2$, $C(O)R^4$, $CH_2CN$, and $CF_3$; wherein $R^3$ is H or $C_{1-6}$ alkyl; and $R^4$ is $C_{1-6}$ alkyl or aryl.

Alternatively, in the compound of Formula 3, n can be 1 or 2, and the $C_{1-6}$ alkyl can be methyl.

The following represents exemplary compounds of the present disclosure:

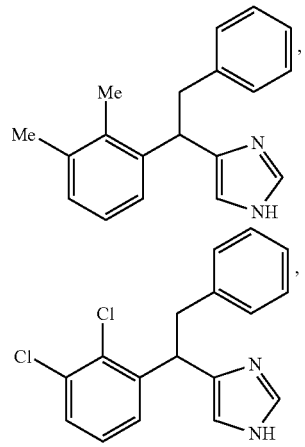

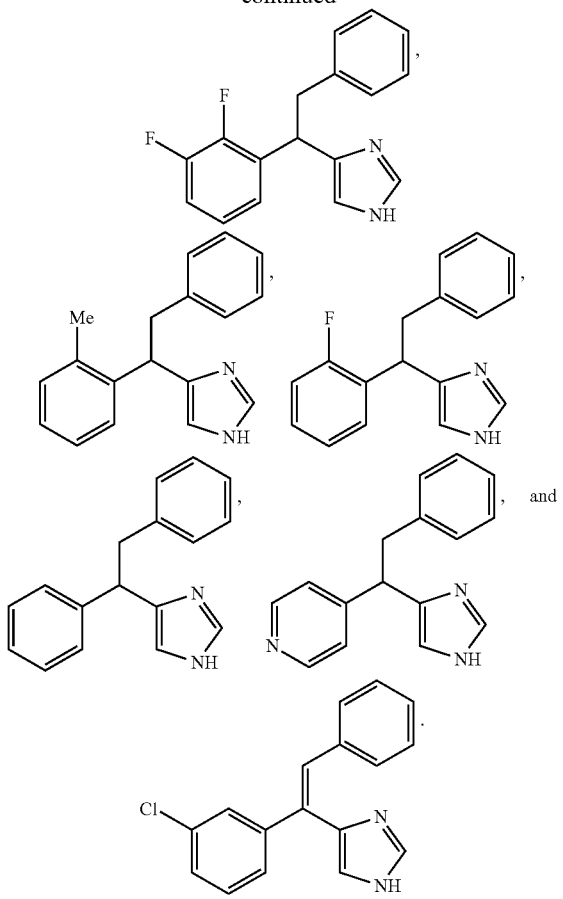

Possible tautomers of the imidazole moieties disclosed herein include:

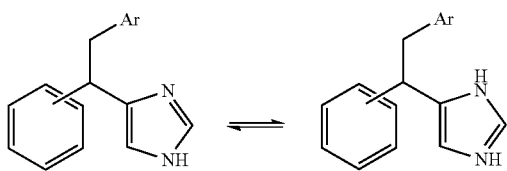

For any structure disclosed herein, the scope of a compound also includes any tautomer which may be formed.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by [tailor this part to the structure being claimed], or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Aryl is an aromatic ring or ring system, including all carbon rings or ring systems such as phenyl, naphthyl, biphenyl, and the like, and heteroaryl. Heteroaryl is an aromatic ring or ring system containing one or more O, N, or S heteroatom. Both aryl and heteroaryl may be substituted or unsubstituted, and unless otherwise indicated, "aryl" and "heteroaryl" should be taken to mean "substituted or unsubstituted aryl" and "substituted or unsubstituted heteroaryl."

Subject to the constraints described herein (e.g. limits on the number of atoms for a substituent), examples of substituents include, but are not limited to:

Hydrocarbyl, meaning a moiety consisting of carbon and hydrogen only, including, but not limited to:

alkyl, meaning hydrocarbyl having no double or triple bonds, including, but not limited to:

linear alkyl, e.g. methyl, ethyl, n-propyl, n-butyl, n-pentyl, n-hexyl, etc., branched alkyl, e.g. iso-propyl, t-butyl and other branched butyl isomers, branched pentyl isomers, etc., cycloalkyl, e.g. cyclopropyl, cyclobutyl, cyclopentyl, cyclohexyl, etc., combinations of linear, branched, and/or cycloalkyl;

alkenyl, e.g. hydrocarbyl having 1 or more double bonds, including linear, branched, or cycloalkenyl alkynyl, e.g. hydrocarbyl having 1 or more triple bonds, including linear, branched, or cycloalkenyl;

combinations of alkyl, alkenyl, and/or akynyl alkyl-CN, such as —$CH_2$—CN, —$(CH_2)_2$—CN; —$(CH_2)_3$—CN, and the like;

hydroxyalkyl, i.e. alkyl-OH, such as hydroxymethyl, hydroxyethyl, and the like;

ether substituents, including —O-alkyl, alkyl-O-alkyl, and the like;

thioether substituents, including —S-alkyl, alkyl-S-alkyl, and the like;

amine substituents, including —$NH_2$, —NH-alkyl, —N-alkyl$^1$alkyl$^2$ (i.e., alkyl$^1$ and alkyl$^2$ are the same or different, and both are attached to N), alkyl-$NH_2$, alkyl-NH-alkyl, alkyl-N-alkyl$^1$alkyl$^2$, and the like;

aminoalkyl, meaning alkyl-amine, such as aminomethyl (—$CH_2$-amine), aminoethyl, and the like;

ester substituents, including —$CO_2$-alkyl, —$CO_2$-phenyl, etc.;

other carbonyl substituents, including aldehydes; ketones, such as acyl (i.e.

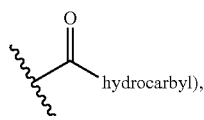

and the like; in particular, acetyl, propionyl, and benzoyl substituents are contemplated;
phenyl or substituted phenyl;
fluorocarbons or hydroflourocarbons such as —CF$_3$, —CH$_2$CF$_3$, etc.; and
—CN;
combinations of the above are also possible, subject to the constraints defined.

Compounds of the present disclosure have the structural formulas depicted in Table 1, which also includes their intrinsic activity potency (nM efficacy (EC50)) to alpha 2a, alpha 2B and alpha 2C receptors. The compound's activity is expressed as its relative efficacy compared to a standard full agonist.

TABLE 1

| Biological Data: Intrinsic Activity Potency nM Efficacy (EC50) | | | |
|---|---|---|---|
| | Alpha 2A | Alpha 2B | Alpha 2C |
| 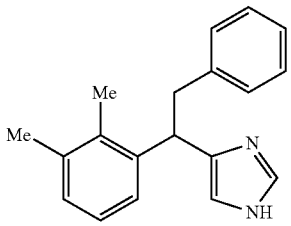 [SMILES: Cc1cccc(C(Cc2ccccc2)c2c[nH]cn2)c1C] | No Data (.28) | 2.09 (1.01) | 26 (.36) |
| 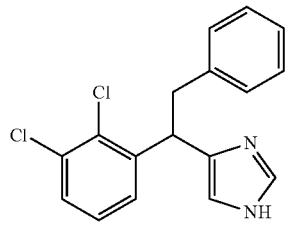 [SMILES: Clc1cccc(C(Cc2ccccc2)c2c[nH]cn2)c1Cl] | No Data (.21) | 8.4 (.97) | 41 (.41) |
| 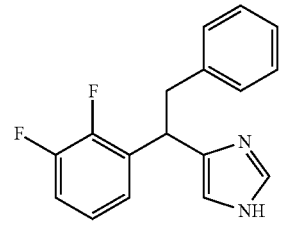 [SMILES: Fc1cccc(C(Cc2ccccc2)c2c[nH]cn2)c1F] | No Data (.04) | 4.4 (.53) | No Data (.17) |
| 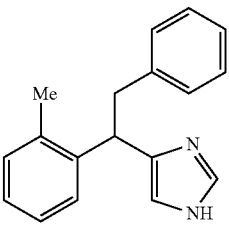 [SMILES: Cc1ccccc1C(Cc1ccccc1)c1c[nH]cn1] | No Data (.10) | 101 (.69) | No Data (.21) |
| 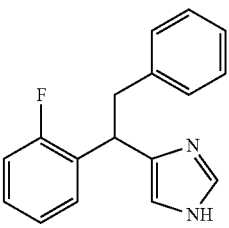 [SMILES: Fc1ccccc1C(Cc1ccccc1)c1c[nH]cn1] | No Data (.04) | 3.5 (.43) | No Data (.18) |

TABLE 1-continued

Biological Data: Intrinsic Activity Potency nM Efficacy (EC50)

| Structure | Alpha 2A | Alpha 2B | Alpha 2C |
|---|---|---|---|
| 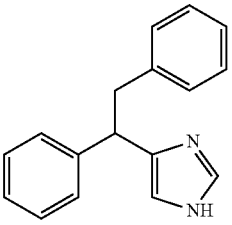 [SMILES: c1ccc(CC(c2ccccc2)c2c[nH]cn2)cc1] | No Data (.05) | 2.8 (.69) | No Data (.10) |
| 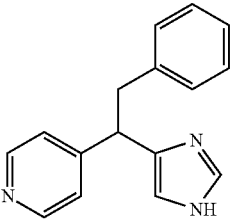 [SMILES: c1ccc(CC(c2ccncc2)c2c[nH]cn2)cc1] | No Data (.02) | 66 (.74) | No Data (.09) |
| 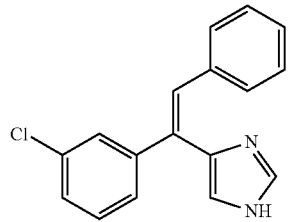 [SMILES: Clc1cccc(/C(=C/c2ccccc2)c2c[nH]cn2)c1] | No Data (.09) | 7.8 (.80) | No Data (.19) |

The compounds disclosed herein are agonists of alpha 2B/2C adrenergic receptors. The alpha 2 receptor activity of the compounds of the present disclosure is demonstrated in an assay entitled Receptor Selection and Amplification technology (RSAT) assay, which is described in the publication by Messier et. al., 1995, Pharmacol. Toxicol. 76, pp. 308-311 (incorporated herein by reference) and is also described below. Another reference pertinent to this assay is Conklin et al. (1993) Nature 363: 274-6, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, $G_q$, elicit this response. Alpha 2 receptors, which normally couple to $G_i$, activate the RSAT response when coexpressed with a hybrid $G_q$ protein that has a $G_i$ receptor recognition domain, called $G_q/i5$.

NIH-3T3 cells are plated at a density of $2\times10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, .E-backward.-galactosidase enzyme activity is determined by adding 200 μl of the chromogenic substrate (consisting of 3.5 mM o-nitrophenyl-beta-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha 2A, alpha 2B and alpha 2C receptors.

Diseases and conditions that may be treated in accordance with the compounds disclosed herein, include, but are not limited to neurodegenerative aspects of the following:

Maculopathies/retinal degeneration diseases and conditions include non-exudative age related macular degeneration (ARMD), exudative age related macular degeneration (ARMD), choroidal neovascularization, diabetic retinopathy, central serous chorioretinopathy, cystoid macular edema, diabetic macular edema and myopic retinal degeneration.

Uveitis/retinitis/choroiditis/other inflammatory diseases and conditions include acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (MEWDS), ocular sarcoidosis, posterior scleritis, serpiginous choroiditis, subretinal fibrosis and uveitis Syndrome, Vogt-Koyanagi-Harada syndrome, punctate inner choroidopathy, acute posterior multifocal placoid pigment epitheliopathy, acute retinal pigment Epheliitis, and acute macular neuroretinopathy.

Vascular Diseases/exudative diseases include diabetic retinopathy, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's Disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease.

Traumatic/surgical/environmental diseases and conditions include sympathetic ophthalmia, uveitic retinal disease, retinal detachment, trauma, laser, PDT, photocoagulation, hypoperfusion during surgery, radiation retinopathy and bone marrow transplant retinopathy. Proliferative disorders include proliferative vitreal retinopathy and epiretinal membranes.

Infectious disorders include ocular histoplasmosis, ocular toxocariasis, presumed ocular histoplasmosis syndrome (PONS), endophthalmitis, toxoplasmosis, retinal diseases associated with HIV Infection, choroidal disease associated with HIV Infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis Genetic disorders include retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum Conditions and diseases associated with retinal tears and holes include retinal detachment, macular hole and giant retinal tear.

Conditions and diseases associated tumors include retinal diseases associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors.

Generally speaking alpha 2 agonists can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other gastrointestinal disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha 2 agonists including alpha 2B/2C agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, and visceral pain.

The compounds are used in accordance with the present disclosure as highly effective analgesics, particularly in chronic pain models, with minimal undesirable side effects, such as sedation and cardiovascular depression, commonly seen with other agonists of the alpha 2 receptors.

The present compounds may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. The actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any pharmacologically acceptable form, such as a tablet, liquid, capsule, powder and the like. However, other routes may be desirable or necessary, particularly if the patient suffers from nausea. Such other routes may include transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the present disclosure is drawn to therapeutic compositions comprising the presently disclosed compounds and a pharmaceutically acceptable carrier. The carrier may be solid, semi-solid, or liquid material that acts as an excipient or vehicle for the active compound. The formulations may also include wetting agents, emulsifying agents, preserving agents, sweetening agents, and/or flavoring agents. If used in an ophthalmic or infusion format, the formulation may contain one or more salts to adjust the osmotic pressure of the formulation.

Another aspect of the present disclosure is drawn to methods for treatment of alpha 2B receptor mediated diseases or conditions through administration of one or more of the presently disclosed compounds.

The alpha 2B receptor mediated diseases or conditions may include but is not limited to glaucoma, elevated intraocular pressure, ischemic neuropathies, optic neuropathy, pain, visceral pain, corneal pain, headache pain, migraine, cancer pain, back pain, irritable bowl syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal of symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, and Parkinson's ALS.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles, the application of even such a light touch or the brush of clothing can be very painful. This condition is termed allodynia and appears to be mediated at least in part by A afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

EXAMPLE A

Method A: Procedure for the preparation of 4-(1-(1H-imidazol-4-yl)-2phenylethyl)pyridine

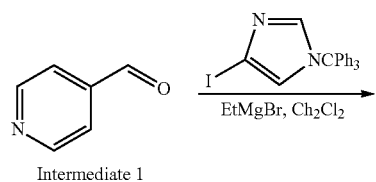

Intermediate 1

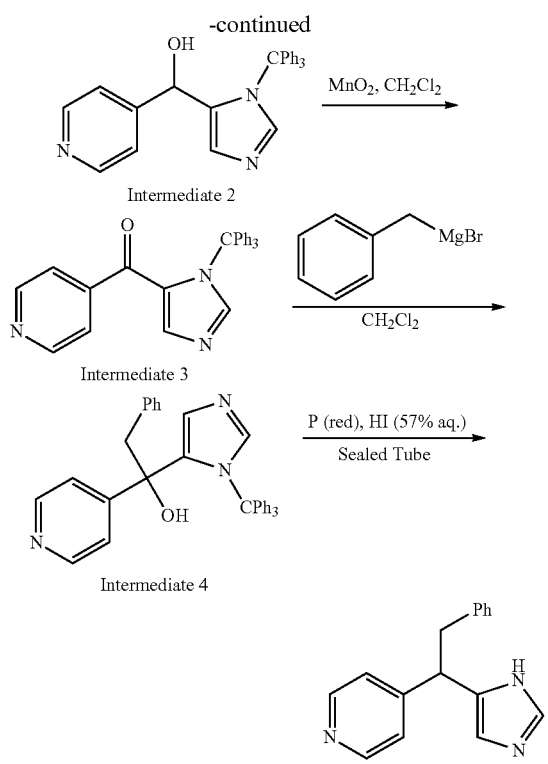

A solution of 4-iodo-1-tritylimidazole (commercially available, 6.1 g, 14.01 mmol) in dichloromethane (30 mL) at −10° C. was treated with ethyl magnesium bromide (4.7 mL, 14.01 mmol, 3M in ether) and allowed to react for 45 m. A solution of pyridine-4-benzaldehyde, (Intermediate 1) (1.2 g, 11.2 mmol) in dichloromethane was added via syringe at −10° C. and stirred for 16 hours at room temperature. The mixture was quenched with water (50 mL) and a saturated solution of ammonium chloride (50 mL). The residue was isolated in a typical aqueous workup and purified by MPLC with 3 to 5% MeOH: $CH_2Cl_2$ to give 2 phenyl-1-(pyridine-4-yl)-1-(1-trityl-1H-imidazo-5-yl)ethanol, (Intermediate 2) as a solid, (3.1 g).

A mixture of 2-phenyl-1-(pyridin-4yl)-1-(1-trityl-1H-imidazol-5-yl)ethanol, (Intermediate 2) (3.1 g, 7.4 mmol) in $CH_2Cl_2$ (60 mL) was treated with manganese (IV) oxide, activated (commercially available from Aldrich) $MnO_2$ (2.9 g, 37.8 mmol) at room temperature. The mixture was heated at 60° C. for 2 hours. The mixture was then cooled to room temperature and filtered through celite and the solvent was removed under vacuum. The residue was purified by MPLC with 3 to 5% MeOH: $CH_2Cl_2$ to give, pyridin-4-yl(1-trityl-1H-imidazol-5-yl)methanone, (Intermediate 3) (3.01 g).

A solution of pyridin-4-yl(1-trityl-1H-imidazol-5-yl) methanone (500 mg, 1.19 mmol) in dichloromethane (25 mL) at room temperature was treated with benzyl magnesium bromide (0.595 mL, 1.78 mmol, 3M in ether) and allowed to react at room temperature and the reaction mixture was then stirred at room temperature for 16 hours. The mixture was quenched with water (20 mL) and a saturated solution of ammonium chloride (20 mL). The residue was isolated in a typical aqueous to give pyridin-4-yl(1-trityl-1H-imidazol-5-yl)methanol, (Intermediate 4) (526 mg, crude).

A mixture of pyridin-4-yl(1-trityl-1H-imidazol-5-yl) methanol, (Intermediate 4) (526 g, 1.03 mmol) in 57% aqueous HI (10 mL) and iPrOH (2 mL) was added red phosphorus (318 mg, 10.3 mmol) in a resealable tube was heated at 160°

C. for 16 h. The mixture was then cooled to room temperature and poured into ice-water, which was then basified with NaOH and diluted with CHCl₃. The residue was isolated in a typical aqueous workup using CHCl3 and purified by MPLC with 5 to 15% MeOH: CH$_2$Cl$_2$ to give 4-(1-(1H-imidazol-5-yl)-2-phenylethyl)pyridine (AGN214418) as a solid, 36 mg. ¹HNMR (CD$_3$OD, 300 MHz) δ 6.98 (s, 1H), 7.20-7.11, (m, 9H), 7.61 (s, 1H), 4.38 (t, J=9 Hz, 1H), 3.43 (dd, J=6 Hz, 12 Hz, 1H), 3.19 (dd, J=9 Hz, 15 Hz, 1H).

EXAMPLE B

Method B: Procedure for the preparation of 4-(1-(2,3-dimethylphenyl)-2-phenylethyl)-1H-imidazole

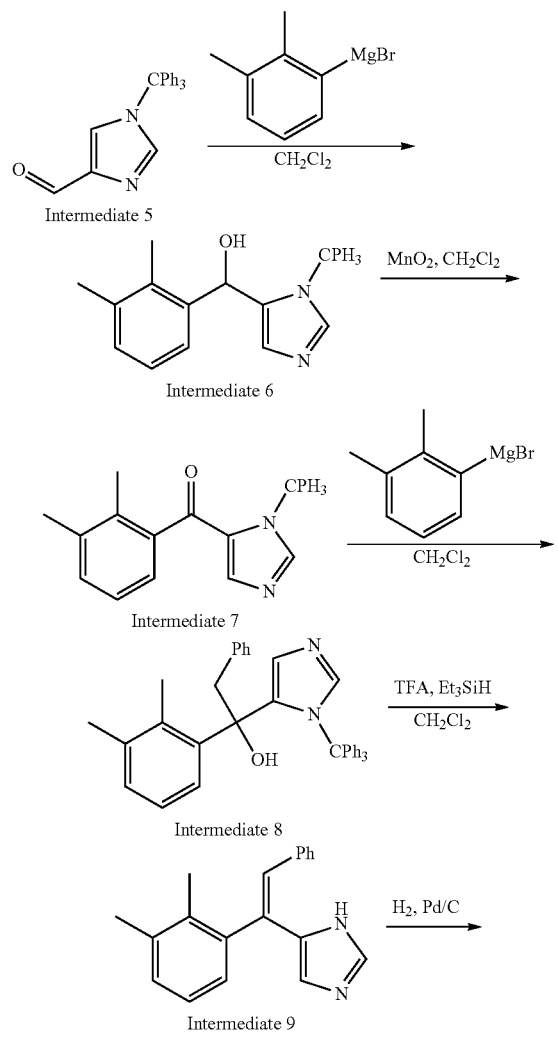

A solution of 1-trityl-IH-imidazole-4-carbaldehyde (commercially available, 2.08 g, 6.15 mmol) in dichloromethane (40 mL) at 0° C. was treated with 2,3-dimethyl magnesium bromide (18.4 mL, 9.2 mmol, 0.5M in THF) and allowed to stir for 16 hours at room temperature. The mixture was quenched with water (50 mL) and a saturated solution of ammonium chloride (50 mL). The residue was isolated in a typical aqueous workup to give (2,3-dimethylphenyl)(1-trityl-IH imidazol-5-yl)methanol, (Intermediate 6) as a solid, (2.8 g, crude).

A mixture of (2,3-dimethylphenyl)(1-trityl-IH-imidazol-5-yl)methanol, (Intermediate 6) (2.4 g, 7.4 mmol) in CH$_2$Cl$_2$ (60 mL) was treated with manganese (IV) oxide, activated (commercially available from Aldrich): MnO$_2$ (2.8 g, 32.3 mmol) at room temperature. The mixture was heated at 60° C. for 2 hours. The mixture was then cooled to room temperature and filtered through celite and the solvent was removed under vacuum. The residue was purified by MPLC with 3 to 5% MeOH:CH$_2$Cl$_2$ to give (2,3-dimethylphenyl)(I-trityl-IH-imidazol-5-yl)methanone, (Intermediate 7), 1.48 g, (62%).

A solution of (2,3-dimethylphenyl)(I-trityl-1H imidazol-5-yl)methanone (450 mg, 1.01 mmol) in dichloromethane (25 mL) at room temperature was treated with benzyl magnesium bromide (1.51 mmol) and allowed to react at room temperature and the reaction mixture was then stirred at room temperature for 5 hours. The mixture was quenched with water (10 mL) and a sat. solution of ammonium chloride (10 mL). The residue was isolated in a typical aqueous to give 1-(2,3-dimethylphenyl)-2-phenyl-1-(1-trityl-1H-imidazol-5-yl)ethanol (Intermediate 8) crude, which was taken to the next step without any purification.

A solution of 1-(2,3-dimethylphenyl)-2-phenyl-l-(1-trityl-1H-imidazol-5-yl)ethanol, (Intermediate 8) crude in dichloromethane (20 mL) was reacted with tiifluoroacetic acid (2 ml) and triethylsilane (0.5 ml) at rt for 24 h. The mixture was evaporated under reduced pressure and quenched with aqueous NaOH. This material was subjected to an aqueous workup and the residue was purified by chromatography on silica gel with 5% NH$_3$-MeOH:CH$_2$Cl$_2$ to yield a mixture of 5-(1-(2,3-dimethylphenyl)-2-phenylvinyl)-1H imidazole(Intermediate 9) (322 mgs).

A mixture of (Intermediates 9) (322 mg) in EtOH (10 mL) was reduced by the action of 10% Pd/C (53 mg) under H$_2$ atmosphere for16 h at rt. The mixture was filtered through Cellos and freed of solvent under reduced pressure. The residue was purified by chromatography on silica gel with 5% NH$_3$-MeOH: CH$_2$Cl$_2$ to give 4-(1-(2,3-dimethylphenyl)-2-phenylethyl)-1H imidazole as a solid, (135 mg) AGN214303.
¹HNMR (CD$_3$OD, 300 MHz) δ 7.55 (s, 1H), 7.14-6.96, (m, 8H), 6.75. (s, 1H), 4.58 (t, J=9 Hz, 1H), 3.43 (dd, J=6 Hz, 12 Hz, 1H), 3.19 (dd, J=9 Hz, 15 Hz, 1H), 2.19 (s, 3H) 2.02 (s, 3H).

EXAMPLE C

Method C: Procedure for the preparation of 4-(1-(2-fluorouhenyl)-2-phenylethyl)-1H-imidazole AGN-217125

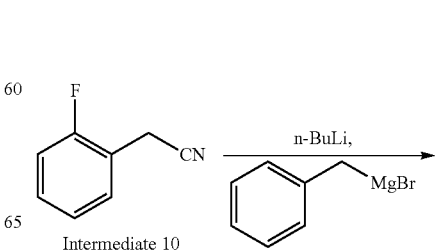

Intermediate 10

EXAMPLE D

Method D: Procedure for the preparation of 4-(1,2-diphenylethyl)-1H-imidazole AGN-217242

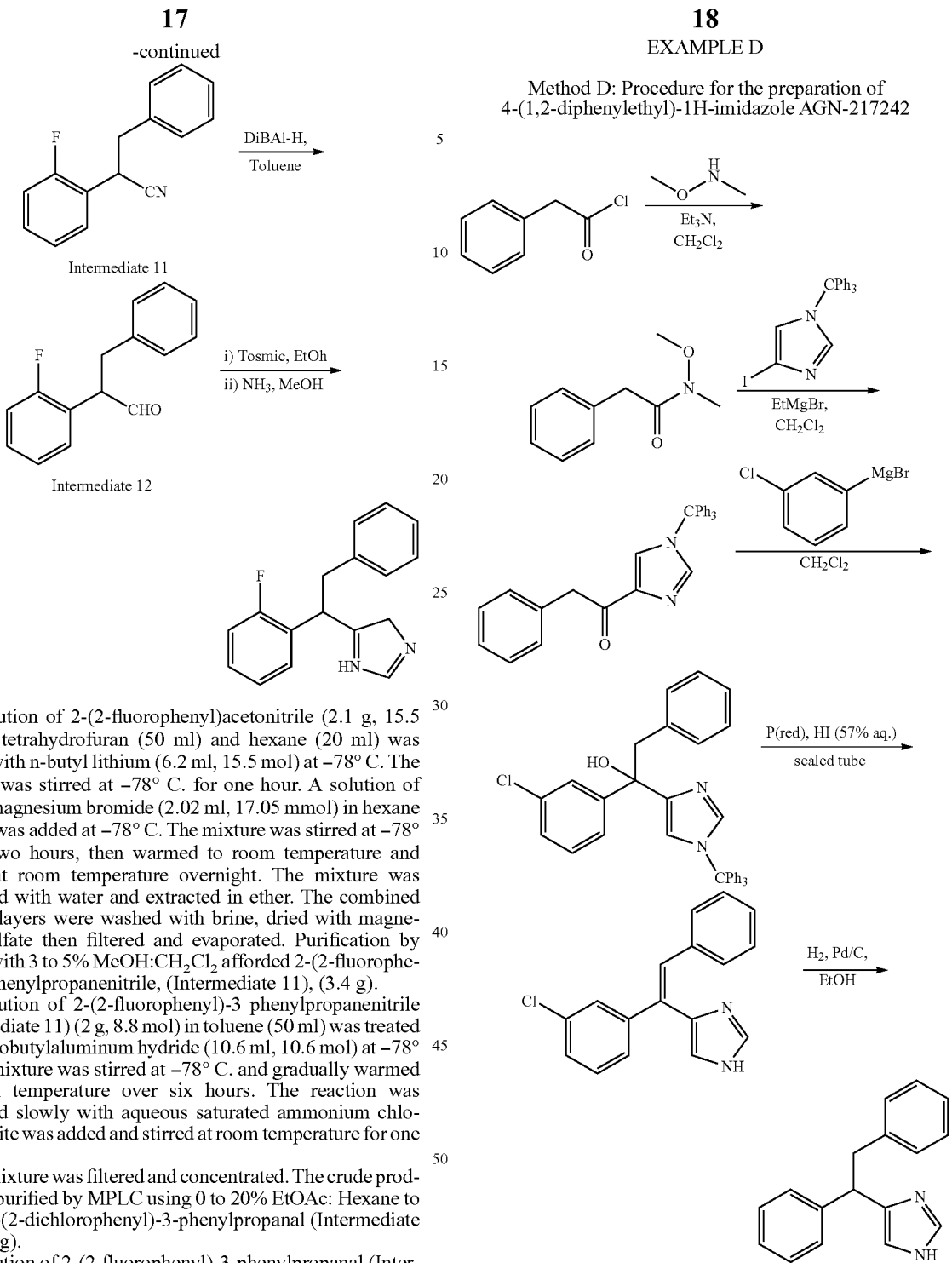

A solution of 2-(2-fluorophenyl)acetonitrile (2.1 g, 15.5 mol) in tetrahydrofuran (50 ml) and hexane (20 ml) was treated with n-butyl lithium (6.2 ml, 15.5 mmol) at −78° C. The mixture was stirred at −78° C. for one hour. A solution of benzyl magnesium bromide (2.02 ml, 17.05 mmol) in hexane (10 ml) was added at −78° C. The mixture was stirred at −78° C. for two hours, then warmed to room temperature and stirred at room temperature overnight. The mixture was quenched with water and extracted in ether. The combined organic layers were washed with brine, dried with magnesium sulfate then filtered and evaporated. Purification by MPLC with 3 to 5% MeOH:$CH_2Cl_2$ afforded 2-(2-fluorophenyl)-3-phenylpropanenitrile, (Intermediate 11), (3.4 g).

A solution of 2-(2-fluorophenyl)-3 phenylpropanenitrile (Intermediate 11) (2 g, 8.8 mol) in toluene (50 ml) was treated with diisobutylaluminum hydride (10.6 ml, 10.6 mol) at −78° C. The mixture was stirred at −78° C. and gradually warmed to room temperature over six hours. The reaction was quenched slowly with aqueous saturated ammonium chloride. Celite was added and stirred at room temperature for one hour.

The mixture was filtered and concentrated. The crude product was purified by MPLC using 0 to 20% EtOAc: Hexane to afford 2-(2-dichlorophenyl)-3-phenylpropanal (Intermediate 12) (1.1 g).

A solution of 2-(2-fluorophenyl)-3-phenylpropanal (Intermediate 12) (707 mg, 3.1 mol) in Ethanol (20 ml) was treated with Tosmic (Tosyl methyl isocyanide) (604 mg, 3.1 mol) at room temperature. The mixture was stirred at room temperature for one hour. The mixture was concentrated in vacuo. The residue was dissolved in Methanol saturated with Ammonia (50 ml) and heated in a sealed tube at 80° C. overnight, cooled to room temperature and the solvent evaporated. Column purification using 0 to 10% Methanol in dichloromethane afforded 350 mg of the product, 4-(1-(2-fluorophenyl)-2-phenylethyl)-1H-imdazole AGN-21712S. $^1$HNMR ($CD_3OD$, 300 MHz) δ 7.57 (s, 1H), 7.33-6.93, (m, 9H), 6.82 (s, 1H), 4.60 (t, J=9 Hz, 1H), 3.43 (dd, J=6 Hz, 12 Hz, 1H), 3.19 (dd, J=9 Hz, 15 Hz, 1H).

A solution of 2-phenylacetyl chloride (commercially available, 4.7 g, 30.5 mmol) in dichloromethane (100 ml) was treated with N,O dimethylhydroxylamine (3.25 g, 33.5 mmol), followed by the addition of triethyl amine (8.5. g 61 mmol) and diaminopyridine (305 mgs). The mixture was stirred at room temperature overnight. The mixture was quenched with water (50 mL) and a saturated solution of ammonium chloride (50 mL). The residue was isolated in a typical aqueous workup and purified by MPLC with 0 to 2% MeOH:$CH_2Cl_2$ to give N-methoxy-N-methyl-2-phenylacetamide, (Intermediate 13) (3.5 g 78.7%).

A solution of 4-iodo-l-tritylimidazole (commercially available, 5.08 g, 13.7 mmol) in dichloromethane (100 mL) at −10° C. was treated with ethylmagnesium bromide (4.5 mL, 13.7 mmol, 3M in ether) and allowed to react for 45 m. A solution of N-methoxy-N-methyl-2-phenylacetamide, (Intermediate 13) (2.0 g, 11.2 mmol) in dichloromethane was added via syringe at −10° C. and stirred for 16 hours at room temperature. The mixture was quenched with water (50 mL) and a saturated solution of ammonium chloride (50 mL). The residue was isolated in a typical aqueous workup and purified by MPLC with 3 to 5% MeOH:$CH_2Cl_2$ to give 2-phenyl-l-(1-trityl-1H-imidazol-4-yl)ethanone, (Intermediate 14) as a solid, (4.65 g).

A solution of 2-phenyl-1-(1-trityl-IH-imidazol-4-yl)ethanone, (Intermediate 14) (595 mg, 1.39 mmol) in dichloromethane (30 mL) at 0° C. was treated with 3-Chlorophenyl magnesium bromide (1 mL, 2.02 mmol, 2M in ether) and allowed to react at room temperature overnight. The mixture was quenched with water (20 mL) and a sat. solution of ammonium chloride (20 mL). The residue was isolated in a typical aqueous workup to give 1-(3-chlorophenyl)-2-phenyl-1-(1-trityl-1H-imidazol-4-yl)ethanol, (Intermediate 15), (469 mg, crude).

A mixture of 1-(3 Chlorophenyl)-2-phenyl-l-(1-trityl-1H-imidazol-4-yl)ethanol, (Intermediate 15) mg; 0.9 mmol) in 57% aqueous HI (10 mL) and iPrOH (2 mL) was added red phosphorus (280 mg, 9.0 mmol) in a resealable tube was heated at 160° C. for 16 h. The mixture was then cooled to room temperature and poured into ice-water, which was then basified with NaOH and diluted with $CHCl_3$. The residue was isolated in a typical aqueous workup using $CHCl_3$ and purified by MPLC with 5 to 15% MeOH:.$CH_2Cl_2$ to give 4-(1-(3-chlorophenyl)-2-phenylvinyl)-1H-imidazole, as a solid, (86 rug), AGN-216677. $^1$HNMR ($CD_3OD$, 300 MHz) δ 7.71 (s, 1H), 7.37-6.96 (m, 9H), 6.55 (s, 1H).

A mixture of 4-(1-(3-chlorophenyl)-2-phenylvinyl)-1H-imidazole (AGN-216677) (35 mg) in EtOH (10 mL) was reduced by the action of 10% Pd/C (20 mg) under $H_2$ atmosphere forl 6 h at rt. The mixture was filtered through Celite and freed of solvent under reduced pressure. The residue was purified by chromatography on silica gel with 5% $NH_3$-MeOH: $CH_2Cl_2$ to give 4-(1,2-diphenylethyl)-1H imidazole as a solid, (31 mg), AGN217242. $^1$H NMR (300 MHz, $CD_3OD$): δ 7.38 (s, 1H), 7.10-7.26 (m, 8H), 7.08 (s, 1H), 4.41 (t, J=9 Hz, 3H), 3.43 (dd; J=9 Hz, 15 Hz, 1H), 3.27 (dd, J=6 Hz, 9 Hz, 1H).

The following compounds have been synthesized by one of the methods described above:

4-(1-(2,3-dichlorophenyl)-2-phenylethyl)-1H-imidazole, AGN-217124:
(Method: A)
$^1$H NMR (300 MHz, $CDCl_3$): δ 7.56 (s, 1H), 7.10-7.19 (m, 8H), 6.75 (s, 1H), 4.87 (t,=9 Hz, 3H), 3.46 (dd, J=6 Hz, 15 Hz, 1H), 3.26 (dd, J=6 Hz, 15 Hz, 1H).

4-(1-(2,3-difluorophenyl)-2-phenylethyl)-1H-imidazole, AGN-217153:
(Method: C)
$^1$H NMR (300 MHz, $CD_3OD$): δ 6.88 (s, 1H), 7.02-7.17 (m, 8H), 7.59 (s, 1H), 4.62 (t, J=9 Hz, 3H), 3.44 (dd, J=6 Hz, 15 Hz, 1H), 3.18 (dd, J=6 Hz, 15 Hz, 1H).

4-(2-phenyl-l-o-tolylvinyl)-1H-imidazole, AGN-216678:
(Method: D)
$^1$H NMR (300 MHz, $CDCl_3$): δ 7.64 (s, 1H), 7.39-6.91 (m, 9H), 6.53 (s, 1H), 2.10 (s, 1H).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of treating a disease or condition, selected from: pain, visceral pain, corneal pain, headache pain, irritable bowel syndrome pain, pain associated with diabetic neuropathy, the treatment of diabetic retinopathy, comprising administering to a mammal in need thereof, a therapeutically effective amount of a compound having Formula 1:

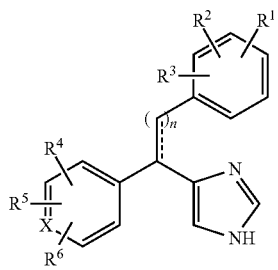

wherein
n=1;
X is C or N;
$R^1$-$R^6$ can be the same or different and are independently selected from the group consisting of $C_{1-6}$ alkyl, $OCH_3$, OH, Cl, Br, $CH_2OH$, $CH_2N(R^7)_2$, $C(O)R^8$, $CH_2CN$, $CF_3$,
wherein $R^7$ is H or $C_{1-6}$ alkyl; and $R^8$ is $C_{1-6}$ alkyl or aryl.

2. The method of claim 1, wherein said $C_{1-6}$ is methyl.

3. The method of claim 1, comprising administering to a mammal in need thereof a therapeutically effective amount of a compound having Formula 2:

Formula 2

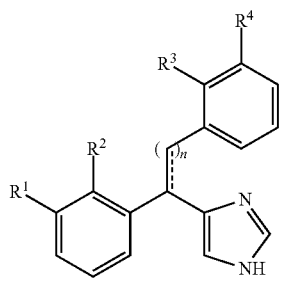

wherein $R^1$-$R^4$ can be same or different and are independently selected from the group consisting of $C_{1-6}$ alkyl, $OCH_3$, OH, Cl, Br, $CH_2OH$, $CH_2N(R^5)_2$, $C(O)R^6$, $CH_2CN$, and $CF_3$;
wherein $R^5$ is H or $C_{1-6}$ alkyl; and
$R^6$ is $C_{1-6}$ alkyl or aryl.

4. The method of claim 1, comprising administering to a mammal in need thereof a therapeutically effective amount of a compound having Formula 3:

Formula 3

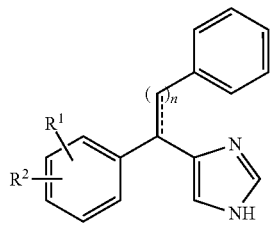

$R^1$-$R^2$ can be same or different and are independently selected from the group consisting of $CH_3$, $C_{1-6}$ alkyl, $OCH_3$, OH, Cl, Br, $CH_2OH$, $CH_2N(R^3)_2$, $C(O)R^4$, $CH_2CN$, and $CF_3$; wherein $R^3$ is H or $C_{1-6}$ alkyl; and $R^4$ is $C_{1-6}$ alkyl or aryl.

5. The method of claim 1, wherein said compound is selected from the group consisting of:

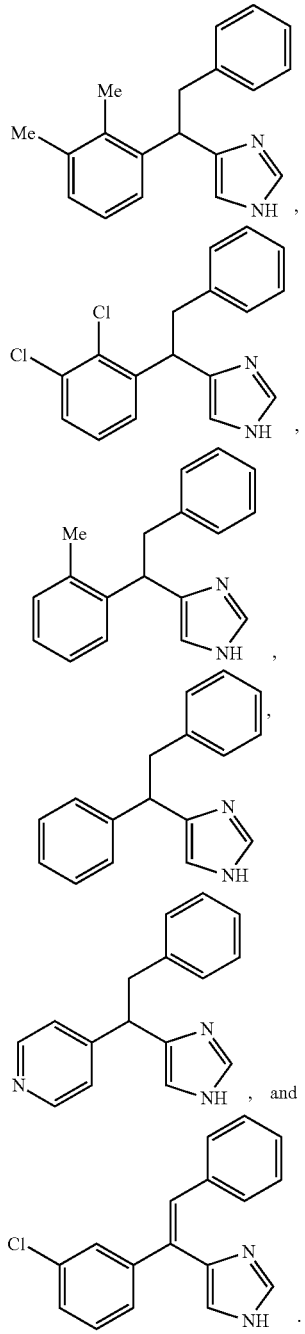

* * * * *

UNITED STATES PATENT AND TRADEMARK OFFICE
CERTIFICATE OF CORRECTION

PATENT NO. : 8,735,438 B2
APPLICATION NO. : 12/966560
DATED : May 27, 2014
INVENTOR(S) : Santosh C. Sinha et al.

It is certified that error appears in the above-identified patent and that said Letters Patent is hereby corrected as shown below:

On the title page, item (56), under "Other Publications", in column 1, line 15, delete "ai," and insert -- al, --, therefor.

On the title page, item (56), under "Other Publications", in column 1, line 16, delete "ai," and insert -- al, --, therefor.

On the title page, item (56), under "Other Publications", in column 1, line 17, delete "Prod rugs" and insert -- Prodrugs --, therefor.

On the title page, item (57), in "Abstract", in column 2, line 11, delete "$CF_3$," and insert -- $CF_3$; --, therefor.

In the Specification

Column 3, line 4, delete "$CF_3$," and insert -- $CF_3$; --, therefor.

Column 3, line 61, delete "$CF_3$," and insert -- $CF_3$; --, therefor.

Column 4, line 19, delete "$C(O)R^6CH_2CN$," and insert -- $C(O)R^6$, $CH_2CN$, --, therefor.

Column 5, line 40-47, delete " 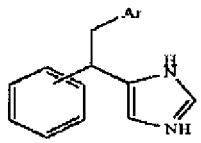 " and insert -- 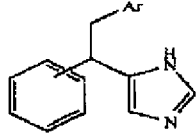 --, therefor.

Column 6, line 49, delete "cycloalkenyl" and insert -- cycloalkenyl; --, therefor.

Column 6, line 52, delete "akynyl" and insert -- alkynyl; --, therefor.

Column 6, line 66, delete "—$CO_2$.phenyl," and insert -- —$CO_2$-phenyl, --, therefor.

Column 8, line 1, delete "hydroflourocarbons" and insert -- hydrofluorocarbons --, therefor.

Column 8, line 9, delete "2a," and insert -- 2A, --, therefor.

Column 11, line 23, delete "(PONS)," and insert -- (POHS), --, therefor.

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,735,438 B2

Column 11, line 29, after "myiasis" insert -- . --.

Column 11, line 36-37, delete "elasticum" and insert -- elasticum. --, therefor.

Column 12, line 2, delete "(hyperhydrosis)" and insert -- (hyperhidrosis) --, therefor.

Column 12, line 63, delete "bowl" and insert -- bowel --, therefor.

Column 13, line 56, delete "2phenylethyl" and insert -- 2-phenylethyl --, therefor.

Column 14, line 41, delete "2 phenyl" and insert -- 2-phenyl --, therefor.

Column 14, line 42, delete "imidazo" and insert -- imidazol --, therefor.

Column 14, line 44, delete "4yl" and insert -- 4-yl --, therefor.

Column 15, line 65, delete "IH" and insert -- 1H --, therefor.

Column 16, line 6, delete "IH imidazol" and insert -- 1H-imidazol --, therefor.

Column 16, line 8, delete "IH" and insert -- 1H --, therefor.

Column 16, line 16 (Approx.), delete "I-trityl-IH" and insert -- 1-trityl-1H --, therefor.

Column 16, line 19, delete "I-trityl-IH imidazol" and insert -- 1-trityl-1H-imidazol --, therefor.

Column 16, line 30, delete "-l-" and insert -- -1- --, therefor.

Column 16, line 32, delete "tiifluoroacetic" and insert -- trifluoroacetic --, therefor.

Column 16, line 38-39, delete "1H imidazole(Intermediate" and insert -- 1H-imidazole, (Intermediate --, therefor.

Column 16, line 42, delete "for16" and insert -- for 16 --, therefor.

Column 16, line 46, delete "1H imidazole" and insert -- 1H-imidazole --, therefor.

Column 16, line 48, delete "6.75." and insert -- 6.75, --, therefor.

Column 16, line 49, delete "3H)" and insert -- 3H), --, therefor.

Column 16, line 55, delete "fluorouhenyl" and insert -- fluorophenyl --, therefor.

Column 17, line 43, delete "3 phenylpropanenitrile" and insert -- 3-phenylpropanenitrile --, therefor.

Column 17, line 63, delete "fiuorophenyl" and insert -- fluorophenyl --, therefor.

Column 17, line 64, delete "imdazole" and insert -- imidazole --, therefor.

Column 18, line 58, delete "N,O dimethylhydroxylamine" and insert -- N,O-dimethylhydroxylamine --, therefor.

Column 18, line 66, delete "-l-" and insert -- -1- --, therefor.

Column 19, line 9, delete "-l-" and insert -- -1- --, therefor.

Column 19, line 12, delete "IH" and insert -- 1H --, therefor.

Column 19, line 21, delete "3 Chlorophenyl" and insert -- 3-Chlorophenyl --, therefor.

Column 19, line 21, delete "-l-" and insert -- -1- --, therefor.

Column 19, line 31, delete "(86 rug)," and insert -- (86 mg), --, therefor.

Column 19, line 35, delete "forl 6" and insert -- for 16 --, therefor.

Column 19, line 38, delete "1H imidazole" and insert -- 1H-imidazole --, therefor.

Column 19, line 49, delete "(t," and insert -- (t, J --, therefor.

Column 19, line 57, delete "-l-" and insert -- -1- --, therefor.

In the Claims

Column 21, line 25, in Claim 1, delete "$CF_3$," and insert -- $CF_3$; --, therefor.

Column 21, line 29, in Claim 3, delete "there of" and insert -- thereof --, therefor.